(12) United States Patent
Gasche et al.

(10) Patent No.: US 8,287,447 B2
(45) Date of Patent: Oct. 16, 2012

(54) OUTER TUBE FOR NATURAL ORIFICE SURGERY

(75) Inventors: Christoph Gasche, Klosterneuburg (AT); Stephen Graham Bell, Rome (IT); Wayne A. Noda, Mission Viejo, CA (US); Bradley J. Sharp, Irvine, CA (US)

(73) Assignee: Minos Medical, Irvine, CA (US)

( * ) Notice: Subject to any disclaimer, the term of this patent is extended or adjusted under 35 U.S.C. 154(b) by 1193 days.

(21) Appl. No.: 11/846,730

(22) Filed: Aug. 29, 2007

(65) Prior Publication Data

US 2009/0062837 A1 Mar. 5, 2009

(51) Int. Cl.
*A61B 1/04* (2006.01)

(52) U.S. Cl. ........ 600/114; 600/121; 600/123; 600/127; 600/129; 600/139

(58) Field of Classification Search .......... 600/114–115, 600/121–125, 139–140
See application file for complete search history.

(56) References Cited

U.S. PATENT DOCUMENTS

| | | | |
|---|---|---|---|
| 4,690,175 A * | 9/1987 | Ouchi et al. | 138/131 |
| 4,825,259 A * | 4/1989 | Berry, Jr. | 356/241.4 |
| 4,886,049 A * | 12/1989 | Darras | 600/124 |
| 5,020,543 A * | 6/1991 | Rothenberg et al. | 600/573 |
| 5,279,610 A * | 1/1994 | Park et al. | 606/108 |
| 5,342,315 A | 8/1994 | Rowe et al. | |
| 5,448,988 A * | 9/1995 | Watanabe | 600/139 |
| 5,533,985 A * | 7/1996 | Wang | 604/264 |
| 5,573,493 A * | 11/1996 | Sauer et al. | 600/121 |
| 5,620,408 A * | 4/1997 | Vennes et al. | 600/114 |
| 5,653,677 A * | 8/1997 | Okada et al. | 600/112 |
| 5,735,792 A * | 4/1998 | Vanden Hoek et al. | 600/138 |
| 5,779,624 A * | 7/1998 | Chang | 600/114 |
| 5,817,061 A * | 10/1998 | Goodwin et al. | 604/164.03 |
| 5,941,815 A | 8/1999 | Chang | |
| 5,989,230 A * | 11/1999 | Frassica | 604/264 |
| 6,107,004 A * | 8/2000 | Donadio, III | 430/320 |
| 6,440,061 B1 * | 8/2002 | Wenner et al. | 600/114 |
| 6,599,237 B1 * | 7/2003 | Singh | 600/114 |
| 6,953,431 B2 * | 10/2005 | Barthel | 600/116 |
| 6,986,738 B2 * | 1/2006 | Glukhovsky et al. | 600/109 |
| 2004/0138529 A1 * | 7/2004 | Wiltshire et al. | 600/144 |
| 2005/0159648 A1 * | 7/2005 | Freed | 600/159 |
| 2005/0267331 A1 * | 12/2005 | Secrest et al. | 600/114 |
| 2006/0241344 A1 | 10/2006 | Wilk | |
| 2007/0106213 A1 | 5/2007 | Spera et al. | |
| 2007/0135803 A1 | 6/2007 | Belson | |

FOREIGN PATENT DOCUMENTS

WO WO 01/70097 9/2001
WO WO 02/069841 A3 9/2002

* cited by examiner

*Primary Examiner* — Matthew J Kasztejna
(74) *Attorney, Agent, or Firm* — John L. Rogitz

(57) ABSTRACT

An outer tube for natural orifice surgery. The outer tube can have interchangeable inserts to establish a desired size and number of lumens. A distal tapered soft plastic plug may be provided to cover the distal end of the tube. Different segments of the tube may have different stiffness characteristics.

6 Claims, 4 Drawing Sheets

OUTER TUBE FOR NATURAL ORIFICE SURGERY

FIELD OF THE INVENTION

The present invention relates generally to systems and methods for transanal and transoral surgical procedures such as for the resolution of appendicitis, gall bladder maladies, and diverticula.

BACKGROUND OF THE INVENTION

In the present assignee's U.S. patent application Ser. Nos. 11/601,199, 11/606,742, and 11/788,597, all of which are incorporated herein by reference, devices and methods are disclosed for natural orifice procedures. Specifically, devices and methods are disclosed in which a medical instrument is advanced through the mouth or anus of a patient to resolve maladies with organs such as the gall bladder and appendix, and to treat diverticulosis. As understood herein, such procedures can be facilitated by using a relatively large outer tube through which one or more instruments such as endoscopes, e.g., colonoscopes, may be advanced to facilitate the desired procedure. It is to such outer tubes that the present invention is directed.

SUMMARY OF THE INVENTION

An assembly for natural orifice surge includes an elongated flexible outer tube defining a single main lumen. An insert is slidably engageable with the main lumen. The insert defines one or more sub-lumens and substantially radially fills the main lumen. The sub-lumen is configured for slidably receiving an endoscope.

If desired, the assembly may include a second insert that is interchangeable with the first insert to define a number of sub-lumens different from the number of sub-lumens defined by the first insert. The reason for the multiple lumens in non-limiting embodiments is to prevent instruments from being twisted and entangled with each other.

In some embodiments, the outer tube defines an open distal end, and the assembly includes a distal plug radially filling the distal end around an outer diameter of the plug. The distal plug can be made of soft non-absorbable plastic, and it tapers distally. The distal plug may be hollow and may have an exterior contour that is frusto-conical or rounded. In non-limiting implementations a tether can be attached to the plug, and the plug can be pushed away from the outer tube to disengage it from the outer tube with the tether facilitating retrieval of the plug from the patient. The distal plug may be defined by the insert itself, which can extend substantially the entire length of the outer tube.

In non-limiting embodiments the distal segment of the tube is more flexible than the proximal segment. This may be attained by rendering the tube out of a sheath having a strengthening coil wound therein, with the distal segment having fewer turns of coil per inch than the proximal segment. In addition or in lieu of the difference in the number of turns, the portion of the sheath around the distal segment can have a hardness that is less than the hardness of the portion of the sheath around the proximal portion. Instead of differing hardnesses, a constant hardness may be used with the distal portion having a thinner wall than the proximal portion.

In another aspect, an assembly for natural orifice surgery includes an elongated flexible outer tube defining a single main lumen. The tube has an outer diameter of about twenty two millimeters and a length of about one hundred centimeters to facilitate placement in a patient through the anus into the colon.

In still another aspect, an assembly for natural orifice surgery includes an elongated flexible outer tube defining a single main lumen. The outer tube defines a distal segment that is contiguous to a proximal segment, and the distal segment is more flexible than the proximal segment.

In yet another aspect, an assembly for natural orifice surgery includes an elongated flexible outer tube defining a single main lumen. The outer tube defines an open distal end. A distal plug radially fills the distal end around an outer diameter of the plug. The plug is made of non-absorbable plastic and tapers distally.

In another aspect, a forward-viewing endoscope is advanced through the anal orifice of a patient to the caecum, and then an outer tube is advanced over the forward-viewing endoscope. The forward-viewing endoscope is removed from the patient and a side-viewing endoscope is then advanced through the outer tube to the caecum. The side-viewing endoscope provides an image of an intended body site.

The details of the present invention, both as to its structure and operation, can best be understood in reference to the accompanying drawings, in which like reference numerals refer to like parts, and in which:

DETAILED DESCRIPTION OF THE PREFERRED EMBODIMENT

Figure 1:
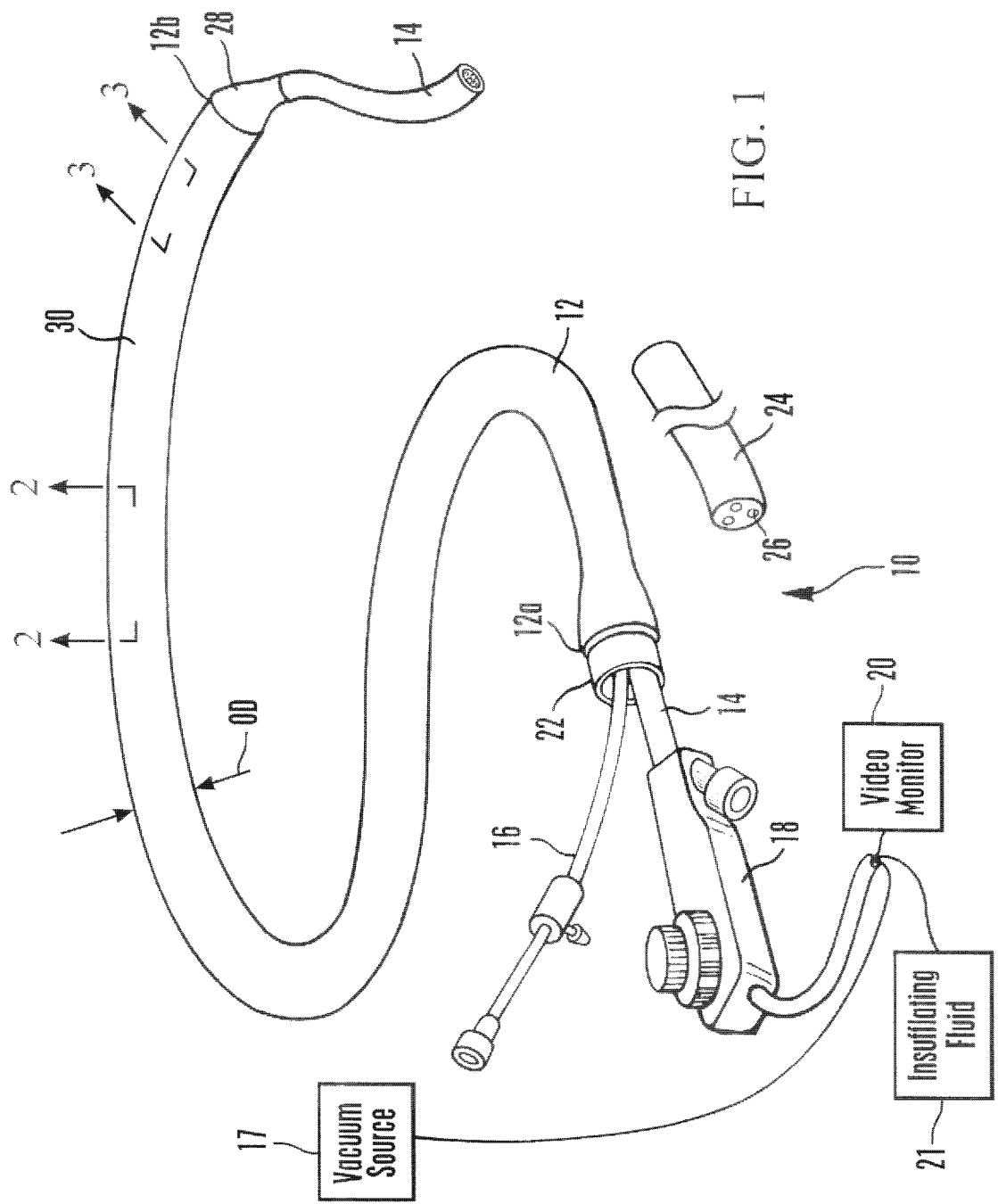
FIG. 1 is a perspective view showing the outer tube, an insert holding medical instruments, and a distal plug, with a replacement insert shown nearby the outer tube.

Referring initially to FIG. 1, an assembly is shown, generally designated 10, that includes a flexible hollow outer tube 12 fixedly or slidably holding one or more components such as but not limited to an endoscope 14 such as a colonoscope and an ancillary catheter 16, either one of which catheters may be connected to a source 17 of vacuum. The endoscope 14 may extend from the open distal end 12b of the outer tube 12 as shown to an endoscope control hub 18 that is external to the patient. In this way, for example, images of the colon from the endoscope 14 can be presented on a monitor 20 to a surgeon. Additional components, e.g., a source 21 of insufflating fluid, may extend through or be engaged with additional working lumens of the endoscope 14 and/or may be swapped according to the stage of the procedure for the components 14, 16. The additional components may include catheters for inverting diverticula into the intestinal lumen, transmural suturing/clipping devices, detachable ligating devices, and polypectomy snares.

The outer tube 12 may have a length of about one hundred centimeters from its open proximal end 12a to its open distal end 12b, and may have a constant outside diameter "OD" of about twenty millimeters. With this length, the tube 12 can extend completely from the anal orifice of an adult patient to the caecum, as opposed to ending at the sigmoid colon, thereby providing a pathway for advancing an instrument such as an endoscope all the way from the natural orifice to the caecum. As set forth further below, the outer tube, 12 may be made from a transparent polyvinylchloride (PVC) plastisol material with stainless steel reinforcing coil embedded therein. The coil may have a diameter of about sixteen mils. The transparent plastic body permits visualization of tissue that may have been retracted into the tube 12 as well as illumination through the tube 12 to illuminate the surgical area.

The components 14, 16 may extend through respective working lumens of the outer tube 12, but in the embodiment shown the components 14, 16 extend through respective working lumens of a flexible insert 22 that, except for its lumens, substantially fills the outer tube 12, both radially and longitudinally. That is, the insert 22 is closely received in the large single central opening of the outer tube 12, and may be replaced by a substitute insert 24 that has three working lumens 26 as shown. Any number of inserts may be provided, so that a user can easily configure the assembly 10 to have as many or as few working lumens as desired, with desired sizes for the working lumens, simply by selecting the appropriate insert and engaging it with the outer tube 12.

Because only two instruments are intended to be used in the non-limiting application shown, the insert 22 has only two working lumens as shown which advantageously closely receive their respective components 14, 16. The insert 22 may otherwise be solid except for the working lumens.

As also shown in FIG. 1, the open distal end of the outer tube 12 may be filled by a distal plug 28 that can be tapered and that can also be hollow if desired so that, e.g., the endoscope 14 can extend out of it. The distal plug 28 may be separate from the insert 22 or may be made integral therewith, and may be made of a soft thermoplastic such as urethane that does not absorb water. The distal plug 28 preferably fits loosely in the catheter and glides easily over a scope. A lubricant 30 such as K-Y jelly or other hydrogel may coat the outside of the outer tube 12 to facilitate placement in the colon. The lubricant 30 may also coat one or more of the lumens described herein.

Figure 2:
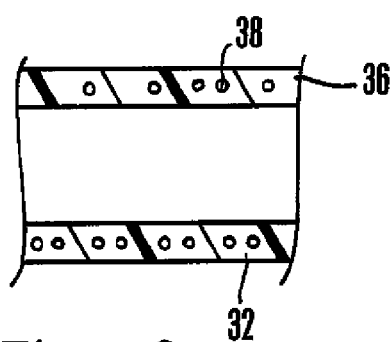
FIG. 2 is a cross-section as seen along the line 2-2 in FIG. 1.
Figure 3:
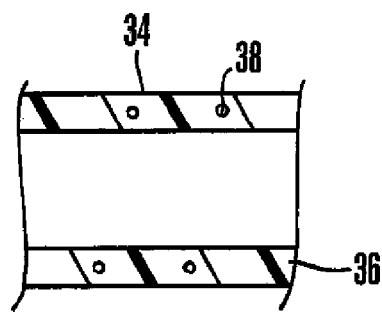
FIG. 3 is a cross-section as seen along the line 3-3 in FIG. 1.

FIGS. 2 and 3 show that the outer tube 12 may have differing flexibility along different segments. More specifically, the proximal portion 32 of the outer tube 12 may be stiffer, i.e., less flexible, than the distal-most segment 34, which may be around ten centimeters in length. The distal segment 34 is relatively more flexible for initiating turns, while the proximal portion 32, while retaining some flexibility, retains adequate column strength and hoop strength for torque control and to prevent kinking and collapse.

In one implementation, the outer tube 12 includes a cylindrical sheath 36 made of, e.g., polyvinylchloride (PVC) plastisol, in which is embedded a stainless steel reinforcing coil 38. As shown in cross-reference to FIGS. 2 and 3, in the proximal portion 32, the coil 38 has less spacing between adjacent loops than it has in the distal segment 34. That is, the distal segment 34 has fewer turns of coil per inch than the proximal segment. Furthermore, the sheath 36 of the proximal portion 32 may be harder than it is around the distal segment 34. In one non-limiting implementation the sheath 36 has a 60 Shore A hardness around the proximal portion 32 and a 45 Shore A hardness around the distal segment 34.

One non-limiting method for making the tube 12 is to wind the coil onto a mandrel in the desired number(s) of turns per inch, then dip the mandrel into liquid plastic for each of the proximal and distal segments, then bond the segments together. Or, when the same hardness plastic but differing thicknesses are used, the mandrel with coil is dipped into the liquid plastic in a way that results in differing thicknesses of plastic, rendering the proximal and distal segments unitary with each other.

Figure 4:
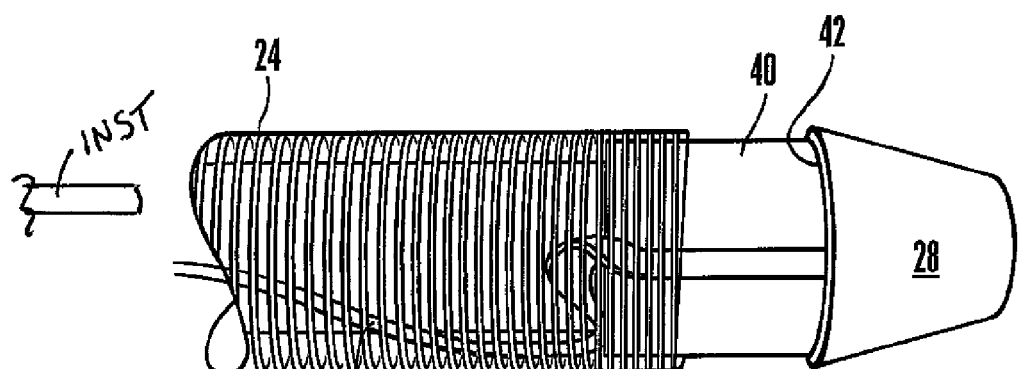
FIGS. 4 and 5 are side views of two embodiments of the distal plug, also showing, through the transparent outer tube, a tether attached to each plug, with the plug in FIG. 4 shown pushed part way out of the tube.

FIG. 4 shows additional details of the distal segment 34 of the outer tube 12. As shown, the distal plug 28 is frusto-conical in shape, and may include a cylindrical stalk portion 40 that can be advanced into the open distal end of the outer tube 12 to engage the interior of the distal segment 24 in an interference fit. FIG. 4 depicts the plug 28 pushed part way out of the tube 12, it being understood that a lip 42 formed between the frusto-conical and cylindrical portions can abut the periphery of the distal end of the tube 12 when the plug 28 is positioned as intended.

A user can advanced an instrument INST through the tube 12 to dislodge the plug 28 from the tube 12 if desired, to, e.g., establish access to the bowel through the now-open distal end of the tube. To this end, a tether 44, which can be seen through the transparent wall of the tube 12, can be attached to the plug 28, so that a gripper or forceps or other instrument can be used after the tube 12 is removed from the patient to retrieve the plug 28 from the patient. Alternatively, the tether can be attached to the tube so that plug retrieval is accomplished when the tube is withdrawn from the colon.

Figure 5:
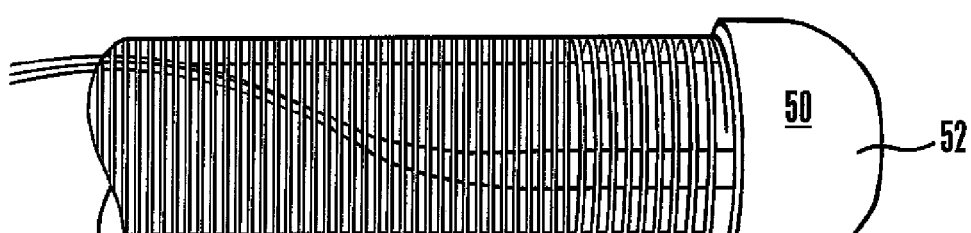

FIG. 5 shows an alternate distal plug 50 that can have a rounded shape as shown, tapering down to a substantially flat distal face 52. Both distal plugs in FIGS. 4 and 5 prevent tissue entrapment and provide a smooth leading edge for ease of pushing the outer tube 12 through the bowel.

Figure 6:
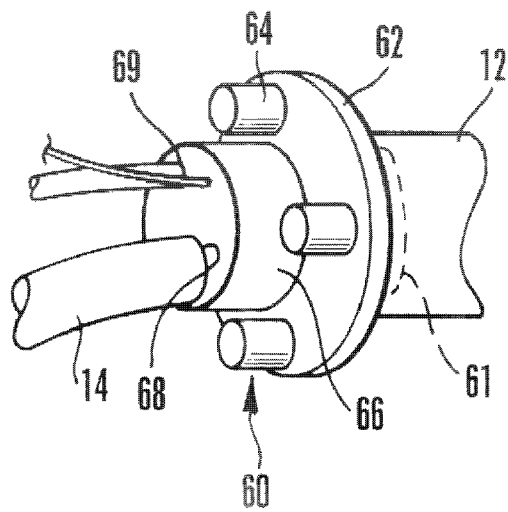
FIG. 6 is a perspective view of the proximal end of an alternate overtube having a proximal plug with handle instead of an insert, with portions of the replacement insert broken away for clarity.

FIG. 6 shows a proximal handle 60 that can be advanced into the open proximal end (single main lumen) of the outer tube 12 to adapt the open proximal end for a smaller instrument. It is to be understood that the handle 60 may simply include a short cylindrical plug 61 (shown in phantom in FIG. 6) that is engaged with the tube 12 in an interference fit and/or glued thereto, or it may be part of or attached to one of the above-discussed elongated inserts that extend substantially the entire length of the tube 12. One of the above-discussed inserts may be advanced through the proximal handle 60 into the outer tube 12.

In the embodiment shown, the handle 60 includes a disk-shaped flange 62 that is radially larger than the tube 12. Four gripping pins 64 extend proximally away from the disk 62 and are substantially equidistantly spaced around the periphery of the disk. A person can gasp the pins 64 to rotate the outer tube 12 as desired.

The handle 60 is hollow, and a disk-shaped adapter cap 66, which may be flexible plastic, is engaged with the disk 62. To this end, the adapter cap 66 may be formed on its distal face with circular protrusions that fit tightly within corresponding grooves in the disk 62.

As shown, the proximal cap 66 forms at least one lumen 68 that is smaller than the large main lumen of the tube 12. The lumen 68 of the proximal cap 66 is sized to fit snugly around, e.g., the endoscope 14 as shown, which may also function as a gas insufflation catheter that may be connected to a source of bowel insufflating fluid or the vacuum catheter 16 shown in FIG. 1. In either case, a seal is formed around the catheter and small lumen 68, so that, e.g., if insufflating gas is infused into the bowel through a catheter extending through the cap 66, it will not easily leak out of the outer tube 12. Similarly, if the vacuum catheter 16 is advanced through the cap 66 to the distal end of the outer tube 12 to evacuate tissue into the tube 12, the vacuum is maintained by the close cooperation of the small lumen 68 with the exterior wall of the vacuum catheter 16. Additional small holes 69 may be provided in the cap for closely receiving guidewires and other components.

Figure 7:
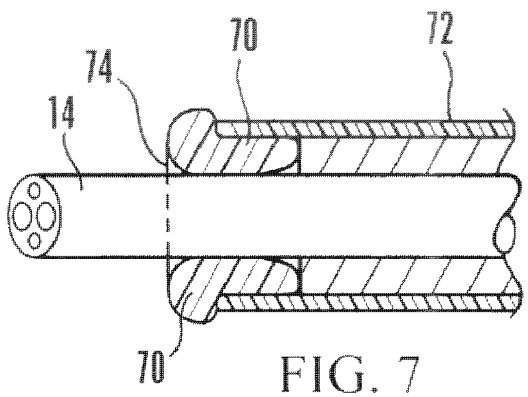
FIGS. 7 and 8 show an alternate balloon-implemented distal plug in the inflated and deflated configurations respectively.
Figure 8:
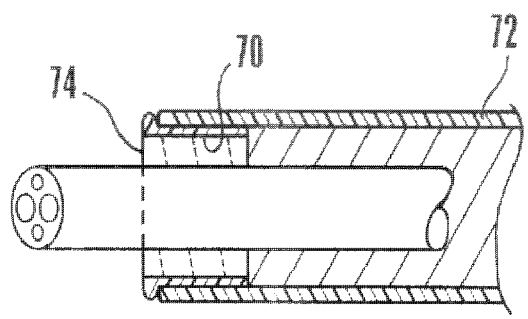

FIGS. 7 and 8 show an alternate distal plug 70 that is engaged with the interior of an outer tube 72 which in all other respects may be identical to the outer tube 12 discussed above. The distal plug 70 may be a toroidal-shaped inflatable structure such as a balloon, and can be adhered to the inside surface of the tube 70 to circumscribe the open distal end 74 of the tube. An instrument such as the above-mentioned endoscope 14 can be advanced through the distal plug 70 which, when inflated, provides a seal between the instrument and the outer tube 72. The balloon can have a variable tightness around the endoscope depending on user-established inflation pressure. A small inflation tube or lumen (not shown) can be provided along the length of the outer tube 72 to provide a pathway for infusing and removing inflation fluid to the plug 70. The plug 70 may be inflated as desired as shown in FIG. 7 to accommodate the diameter of the particular instrument being advanced through the outer tube 72 and then deflated as shown in FIG. 8 to facilitate moving the instrument through the plug 70, into or out of the patient.

Figure 9:
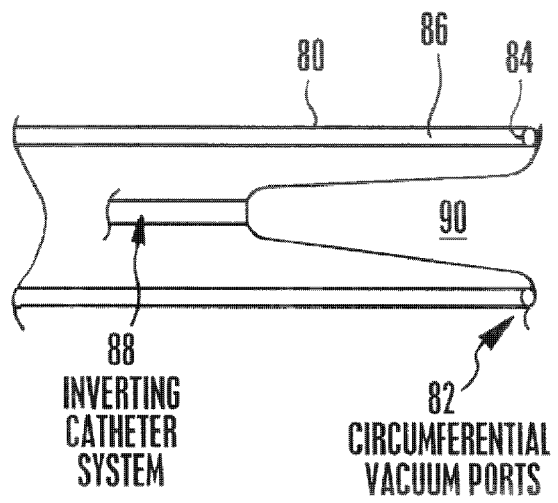
FIG. 9 is a side view of the distal end of an alternate outer tube, with a vacuum ring formed around the periphery of the open distal end.

FIG. 9 shows an outer tube 80 that in all essential respects is identical to the tubes discussed above, except that its circular distal face 82 establishes a circumferential vacuum port. The face 82 may be concave or V-shaped as shown, and one or more vacuum holes 84 can establish fluid communication between the face 82 and a vacuum lumen 86 that can extend the length of the tube 80 and that can communicate with, e.g., the source of vacuum 17 shown in FIG. 1. With this structure, the tube 80 can be positioned against tissue and a vacuum established around its distal end, to facilitate, for example, an inverting catheter system 88 to invert tissue 90 into the tube 80. Details of the inverting catheter system 88 are set forth in one or more of the above-referenced patent applications.

The vacuum seal provided by the circumferential vacuum distal end of the tube 80 stabilizes the tube 80 at the target site and provides a closed chamber for cleansing the surgical site, which is now isolated from the rest of the bowel. It also limits exposure of colonic tissue in the event of unintended perforation.

Figure 10:
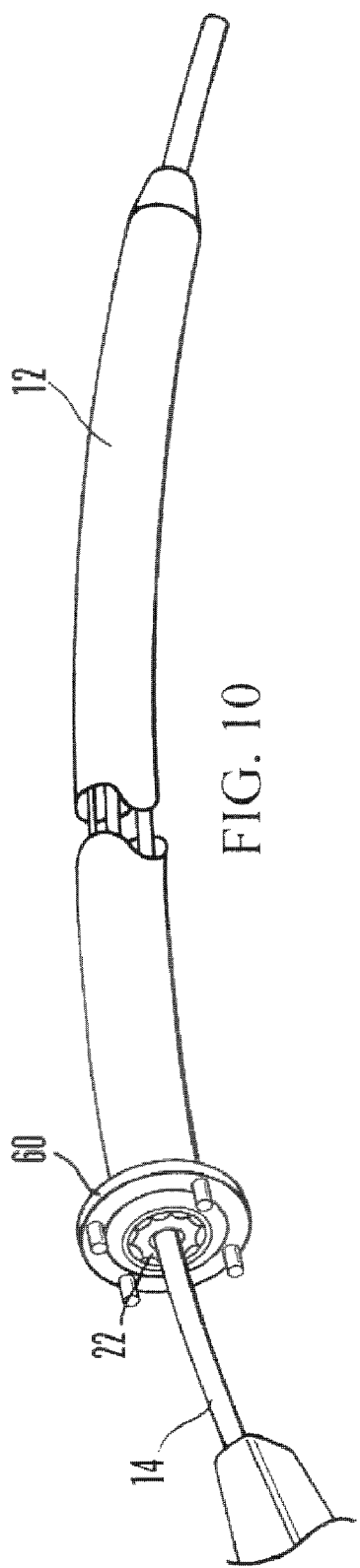
FIG. 10 is a cut-away perspective view of the outer tube, showing an insert completely advanced into the tube through the proximal handle shown in FIG. 6.
Figure 11:
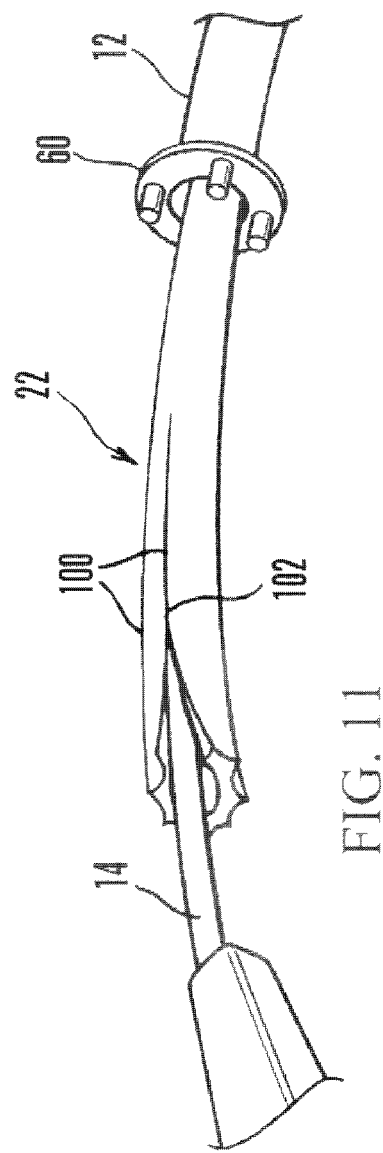
FIG. 11 is a cut-away perspective view of the proximal portion of the outer tube, showing an insert being advanced into the tube to illustrate the longitudinal ribs ad slit of the non-limiting insert.

FIGS. 10 and 11 show that in non-limiting implementations, the insert 22 shown and discussed above may be formed with plural longitudinal ribs 100 that are radially spaced around the otherwise cylindrical body of the insert and that rise radially therefrom, to facilitate engagement of the insert 22 with the outer tube 12. The insert 22 may also be formed with a longitudinal slit 102 as shown, through which access to the interior of the insert 22 may be gained. The slit 102 preferably is biased to be closed.

Figure 12:
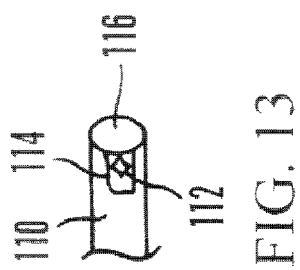
FIG. 12 is a cut-away perspective view showing the distal end of a forward-viewing endoscope.
Figure 13:
FIG. 13 is a cut-away perspective view showing the distal end of a side-viewing endoscope.

FIG. 12 shows that a forward-viewing endoscope 104 include optics 106 that are disposed for imaging space directly in front of the distal end 108 of the endoscope 104. In contrast, FIG. 13 shows that a side-viewing endoscope 110 include optics 112 that are disposed for imaging space through, e.g., a window 114 in the side of the endoscope 110, i.e., space that is lateral to the distal end 116 of the endoscope 110. Or, the side-viewing endoscope may have a distal end bent ninety degrees with respect to the axis of the scope, with optics disposed to image space out of the bent distal end, i.e., space that is lateral to the axis of the scope relative to the organ in which the scope is positioned.

With the above structure, the following non-limiting procedure may be performed. The forward-viewing endoscope 104 may be advanced through the anal orifice of a patient to the caecum. Then, the tube 12 may be advanced over the endoscope 104, and the endoscope 104 removed from the patient. The side-viewing endoscope 110 may then be easily advanced through the tube 12 to the caecum. It will readily be appreciated that the tube 12 facilitates advancing the side-viewing endoscope 110 into the bowel, which would otherwise be rendered more difficult without the tube 12 since the side-viewing scope 110 cannot easily provide a view ahead of where the scope is being pushed.

The side-viewing endoscope 110 is useful for, e.g., viewing for conducting a natural orifice appendectomy in accordance with one or more of the above-referenced patent applications. It may now be appreciated that the removable distal plug 70 may be pushed off the end of the tube 12 when it is desired to invert excised tissue such as an appendix into the tube 12 using a vacuum, with the tube 12 thus providing an advantageously large megalumen in which to draw the tissue.

While the particular OUTER TUBE FOR NATURAL ORIFICE SURGERY is herein shown and described in detail, it is to be understood that the subject matter which is encompassed by the present invention is limited only by the claims.

What is claimed is:
1. An assembly for natural orifice surgery, comprising:
   an elongated flexible outer tube defining a single main lumen;
   a first insert slidably engageable with the main lumen and defining at least one sub-lumen, the first insert substantially radially filling the main lumen, the sub-lumen configured for slidably receiving an endoscope, the first lumen having a first sub-lumen configuration; and
   at least a second insert interchangeable with the first insert and having a sub-lumen configuration different from the first sub-lumen configuration, the inserts being provided together as part of the assembly such that plural inserts are provided to the user with the assembly so that the user can configure the assembly to a number and/or size of working lumens as desired by selecting an appropriate one of the first or second inserts and engaging it with the main lumen of the flexible outer tube;
   wherein the outer tube defines an open distal end, and the assembly comprises a distal plug in the distal end; and
   wherein a tether is attached to the distal plug, the distal plug being pushable away from the outer tube using a surgical instrument to disengage it from the outer tube, the tether facilitating retrieval of the plug from the patient.
2. The assembly of claim 1, wherein the outer tube defines a distal segment contiguous to a proximal segment, the distal segment being more flexible than the proximal segment.

3. The assembly of claim 1, wherein the outer tube is made of a sheath holding a coil, the distal segment having fewer turns of coil per inch than a proximal segment.

4. The assembly of claim 3, wherein the portion of the sheath around the distal segment has a hardness less than the hardness of the portion of the sheath around the proximal segment.

5. The assembly of claim 1, comprising the endoscope.

6. The assembly of claim 1, wherein the insert extends substantially the entire length of the outer tube while accommodating the distal plug in the distal end.

* * * * *